US012125617B2

(12) United States Patent
Griffin et al.

(10) Patent No.: US 12,125,617 B2
(45) Date of Patent: *Oct. 22, 2024

(54) RADIATION CURABLE THERMISTOR ENCAPSULATION

(71) Applicant: DeRoyal Industries, Inc., Powell, TN (US)

(72) Inventors: Sam Griffin, New Tazewell, TN (US); Eduardo Diaz, Costa Rica (CR); Vincent Denis Jardret, Powell, TN (US); Zachary C. Ziegler, Knoxville, TN (US); Ethan Edward Valentine, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/144,314

(22) Filed: May 8, 2023

(65) Prior Publication Data

US 2023/0274865 A1    Aug. 31, 2023

Related U.S. Application Data

(63) Continuation of application No. 16/807,654, filed on Mar. 3, 2020, now Pat. No. 11,682,505.

(51) Int. Cl.
*H01C 17/00* (2006.01)
*A61B 5/00* (2006.01)
(Continued)

(52) U.S. Cl.
CPC ............... *H01C 17/00* (2013.01); *A61B 5/01* (2013.01); *A61B 5/742* (2013.01); *H01C 7/008* (2013.01);
(Continued)

(58) Field of Classification Search
CPC .......... H01C 17/00; H01C 7/008; H01C 1/02; H01C 1/034; H01C 17/02; A61B 5/01;
(Continued)

(56) References Cited

U.S. PATENT DOCUMENTS

| 3,678,751 A | 7/1972 | Mead et al. |
| 3,949,609 A | 4/1976 | Hammerslag |

(Continued)

FOREIGN PATENT DOCUMENTS

| EP | 2175457 A2 | 4/2010 |
| JP | H08102405 A | 4/1996 |
| JP | 2011222782 A | 11/2011 |

OTHER PUBLICATIONS

AZO Materials: LED Curable Adhesive System LED401.
(Continued)

*Primary Examiner* — Jay B Shah
*Assistant Examiner* — Meghan R Kumar
(74) *Attorney, Agent, or Firm* — Luedeka Neely. P.C.

(57) ABSTRACT

A medical temperature monitoring system includes an electrical wire set having a thermistor at a distal end of the wire set configured to sense temperatures to which the thermistor is exposed; an electronic circuit in electrical communication with the wire set and the thermistor and configured to convert the temperatures sensed by the thermistor to temperature display signals; a display in electrical communication with the electronic circuit for receiving the temperature display signals and displaying temperatures corresponding to the temperature display signals; and a bead of cured protective material encapsulating the thermistor. The protective material is a radiation curable adhesive applied to the thermistor in an uncured state and then cured to encapsulate
(Continued)

the thermistor. The bead of cured protective material electrically isolates the conductor sufficient to pass a Hi-Pot test at 500 VAC, <0.1 mA.

17 Claims, 3 Drawing Sheets

(51) Int. Cl.
    *A61B 5/01*     (2006.01)
    *H01C 7/00*     (2006.01)

(52) U.S. Cl.
    CPC . *A61B 2562/0271* (2013.01); *A61B 2562/125* (2013.01); *A61B 2562/162* (2013.01); *A61B 2562/18* (2013.01)

(58) Field of Classification Search
    CPC ............ A61B 5/742; A61B 2562/0271; A61B 2562/125; A61B 2562/162; A61B 2562/18; A61B 2562/12; G01K 1/08; G01K 7/22; G01K 13/20
    See application file for complete search history.

(56) References Cited

U.S. PATENT DOCUMENTS

| | | | |
|---|---|---|---|
| 4,437,084 | A | 3/1984 | Clayton, Jr. |
| 4,623,559 | A | 11/1986 | Hudock |
| 4,955,980 | A | 9/1990 | Masuo |
| 6,082,895 | A | 7/2000 | Janicek |
| 6,880,969 | B2 | 4/2005 | Adachi et al. |
| 8,059,947 | B2 | 11/2011 | Bradley et al. |
| 8,303,173 | B2 | 11/2012 | Bradley et al. |
| 9,370,887 | B2 | 6/2016 | Kloiber et al. |
| 2004/0242976 | A1* | 12/2004 | Abreu ................... A61B 5/746 600/315 |
| 2007/0260300 | A1 | 11/2007 | Gregorich et al. |
| 2010/0004734 | A1 | 1/2010 | Ramzipoor et al. |
| 2010/0260941 | A1 | 10/2010 | Bushmire et al. |
| 2012/0026659 | A1* | 2/2012 | Kim ...................... H01G 4/236 361/679.01 |
| 2015/0034156 | A1 | 2/2015 | Kensicki et al. |
| 2016/0090504 | A1 | 3/2016 | Araki |

OTHER PUBLICATIONS

Dymax: See-Cure Adhesives Selector Guide.
European Patent Office, European Search Report, Application 21764856. 7, Apr. 24, 2024, Munich, Germany.
European Patent Office, Application 21 764 856.7, communication extended European Search Report, Apr. 24, 2024, including Supplementary European Search Report EP 217 648 56.7, 10 date of completion of search Apr. 10, 2024, Munich, Germany.
LED Light Curable Adhesives.
LED403Med Product Information: One component, LED curable system for high performance bonding, sealing, coating and encapsulation.
Masterbond: UV Adhesives.
Masterbond: UV Curing Potting Compounds.
MDDI: The Adhesive Bonding of Medical Devices: Jun. 2001.
Memorandum: Radiation Curable Thermistor Encapsulation Disclosure.
PCT International Searching Authority, Authorized Office Lee Young, Notification of Transmittal of the International Search Report and the Written Opinion of the International Searching Authority, or the Declaration (PCT Rule 44.1); PCT/US21/ 19905 international filing date Feb. 26, 2021, Date of mailing May 21, 2021 (14 pages).
Preliminary Analysis: Overall Presentation of the LED Cured encapsulation of Temperature probe.
Tangent adhesives & more: Encapsulants.
Tangent Adhesives & more: Medical Device Bonding/Coating.
UV Potting Materials for Electronic Application.

* cited by examiner

RADIATION CURABLE THERMISTOR ENCAPSULATION

FIELD

This disclosure relates to the field of temperature sensors. More particularly, this disclosure relates to improved temperature sensors and methods for making temperature sensors, especially for medical applications.

BACKGROUND

A thermistor is a temperature-sensitive resistor. Thermistors are often used as temperature sensors in medical applications. For example, thermistors are utilized to monitor the body temperature of a patient. To protect thermistors from exposure to and interference from unwanted environmental factors, such as humidity/moisture, electrical interference, and other environmental factors commensurate with medical applications, thermistors utilized in medical applications are coated or protected by a protective material.

One conventional protective material is a molded thermoplastic resin cap that is bonded to the thermistor with epoxy as an encapsulate. Although functional, there are drawbacks to this method of protection, especially in their manufacture. First, the caps must be obtained. Also, the caps must be bonded to the thermistors. Bonding is commonly done with a time or heat curable epoxy adhesive by dispensing a quantity of the epoxy adhesive into the cap, placement of the cap onto the sensor with epoxy, mess associated with epoxy, considerable time lost in the curing of the epoxy (typically 8 or more hours), and cleanup of excess epoxy that seeps out during the curing process. Thus, the caps and epoxy represent considerable time and expense and other nuisances. In addition, the use of caps and their application to thermistors can undesirably affect the temperature response of the thermistor.

What is desired is an improved temperature sensor and, in particular, an improved structure and method for making a thermistor having a protective material.

SUMMARY

The current disclosure relates to improved temperature monitoring systems, improved thermistor, and methods for making temperature sensors. In one aspect, a medical temperature monitoring system according to the disclosure includes an electrical wire set having a thermistor at a distal end of the wire set configured to sense temperatures to which the thermistor is exposed; an electronic circuit in electrical communication with the wire set and the thermistor and configured to convert the temperatures sensed by the thermistor to temperature display signals; a display in electrical communication with the electronic circuit for receiving the temperature display signals and displaying temperatures corresponding to the temperature display signals; and a bead of cured protective material encapsulating the thermistor, the protective material comprising a radiation curable adhesive applied to the thermistor in an uncured state and then cured to encapsulate the thermistor, wherein the bead of cured protective material electrically isolates the conductor sufficient to pass a Hi-Pot test at 500 VAC, <0.1 mA.

In another aspect, a thermistor according to the disclosure includes an electrical wire set having a pair of wires with a thermistor at a distal end of the wires configured to sense temperatures to which the thermistor is exposed; and a bead of protective material encapsulating the conductor, the protective material comprising a radiation curable adhesive applied to the thermistor in an uncured state and then cured to encapsulate the thermistor as the bead and isolate the conductor sufficient to pass a Hi-Pot test at 500 VAC, <0.1 mA.

In a further aspect, a method for making a temperature sensor according to the disclosure includes the steps of providing an electrical wire set having a thermistor at a distal end of the wire set configured to sense temperatures to which the thermistor is exposed; providing a protective material comprising a radiation curable adhesive in a liquid uncured state having a viscosity; dipping the thermistor into the protective material at a speed selected for the viscosity of the protective material in the uncured state to uniformly coat the thermistor with the protective material; withdrawing the coated thermistor from the protective material at a speed selected for the viscosity of the protective material in the uncured state while maintaining the thermistor oriented downward to allow for flow of the protective material as coated on the thermistor to be formed into and retained on the thermistor in the configuration of a bead; maintaining the coated thermistor in the downward orientation at a temperature selected to maintain adequate viscosity of the protective material forming the bead to prevent dripping of the bead; and curing the bead of the protective material by exposing the bead to radiation.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 2:
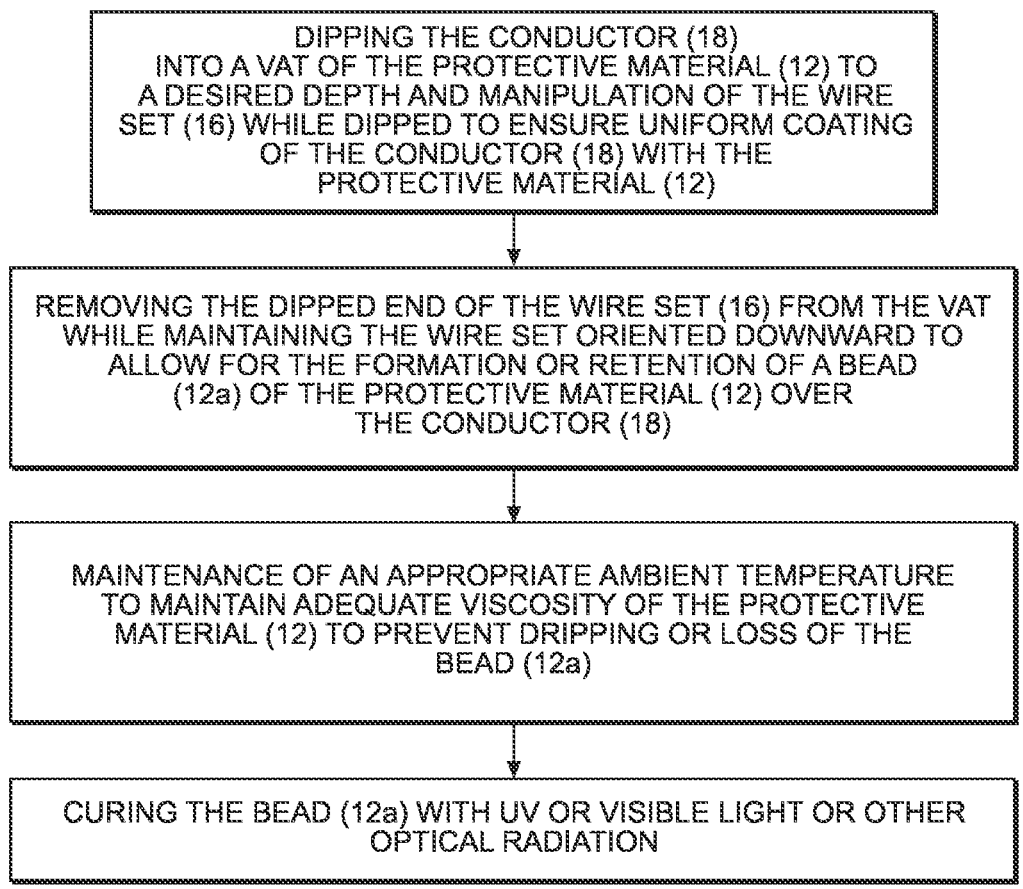
FIG. 2 is a flow chart of the steps shown in FIGS. 1A-1F.
Figure 3:
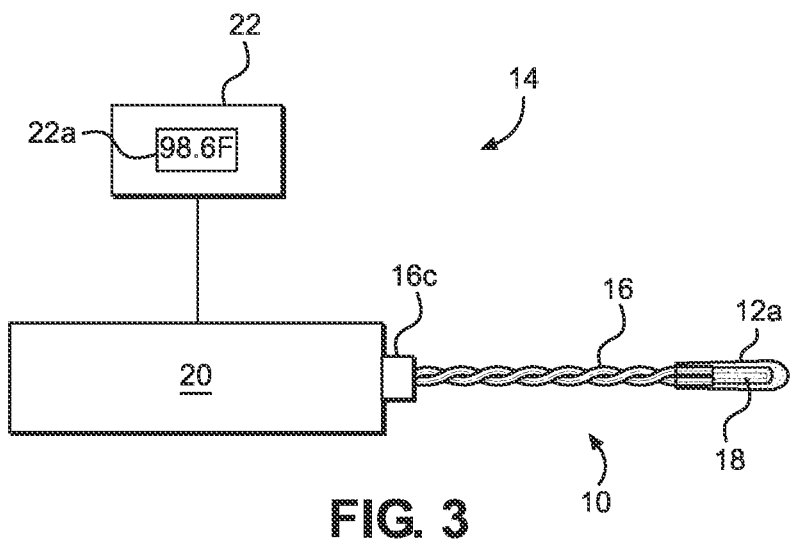
FIG. 3 shows a temperature monitoring system according to the disclosure.

With reference to the drawings, FIGS. 1A-1F depict steps according to a method of the disclosure for coating a temperature sensor 10 with a protective material 12. FIG. 2 is a flow chart of the steps shown in FIGS. 1A-1F. FIG. 3 depicts a temperature monitoring system 14 according to the disclosure utilizing the temperature sensor 10.

The temperature sensor 10 as shown is configured as a thermistor and includes a wire set 16 having a pair of wires 16a and 16b connected at their distal ends to a conductor 18, generally provided by a semiconductor material soldered to the distal ends of the wires 16a and 16b. The conductor 18 may preferably be a semiconductor.

The proximal ends of the wires 16a and 16b are configured to be plugged into or otherwise electrically connected as by a connector 16c to a circuit such as a microprocessor 20 in communication with a display 22. The temperature sensor 10 senses changes in the temperature of the location of the conductor 18. In the case of a thermistor, the resistance of the conductor 16 varies with temperature. Thus, the microprocessor 20 applies a voltage across the conductor 18 via the wire set 16 and measures the current flowing through the wire set 16 in response to the voltage. The resistance of the thermistor varies in response to the temperature. The measured current will vary relative to the change in resistance in accordance with Ohm's law (voltage=current× resistance).

The microprocessor 20 includes hardware and software configured to convert the temperature sensed by the temperature sensor 10 to signals that are compatible with the display 22. The display 22 receives the signals from the microprocessor 20 indicative of the temperature of the location of the conductor 18 and displays a temperature 22a of the location of the conductor 18.

The protective material 12 is provided by a radiation curable adhesive having desired thixotropic properties that render it of desired stability against flow during application of the radiation curable adhesive to the conductor 18. A preferred protective material is a radiation curable adhesive made of an aliphatic urethane acrylate and monomer blend having a viscosity in the uncured state characterized as thixotropic, 9,000 cP-18,000 cP [Brookfield 25 degrees C., 30 RPM]. This preferred radiation curable adhesive is curable by ultraviolet or visible light, with a hardness of Shore D50-65 when cured. The preferred radiation curable adhesive also effectively electrically isolates the conductor 18 from a patient in the cured state and passes a Hi-Pot test at 500 VAC, <0.1 mA. In this Hi-Pot test, the probe is immersed into a water bath electrically connected to a ground pad. A 500 VAC potential is then applied to the thermistor via the probe's conductors. The leakage current flowing through the water bath is then measured. The isolation provided by the curable adhesive in the cured state is considered sufficient when this leakage current is less than 0.1 mA. It has also been observed that the preferred radiation curable adhesive provides similar thermal conductivity characteristics to those of conventional epoxy applied caps such that the thermal response of the resulting temperature sensor is not materially different.

It has been observed that the preferred adhesive used to provide the protective material 12 cures relatively quickly to a quick-set state upon exposure to UV/visible light, e.g., within a few seconds, with a full cure achieved in less than about one minute which facilitates the manufacturing process. The ability to cure using optical radiation such as UV/visible light also simplifies the manufacturing process and reduces hazards to workers. It is also observed that the cured protective material provides suitable protective properties of the conductor 14 from moisture and electrical insulating properties for medical applications such as monitoring patient temperature.

Returning now to FIGS. 1A-1F and FIG. 2, there are shown steps according to a method of the disclosure for coating the wire set 16 with the conductor 18 with the protective material 12 to provide the temperature sensor 10.

Figure 1A:
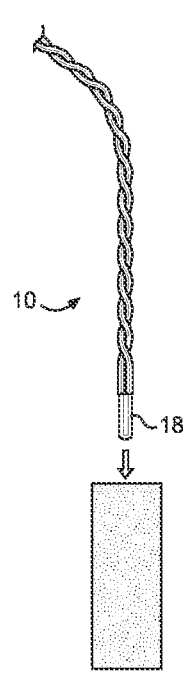
FIGS. 1A-1F depict steps according to a method of the disclosure for coating temperature sensors with a protective material.
Figure 1B:
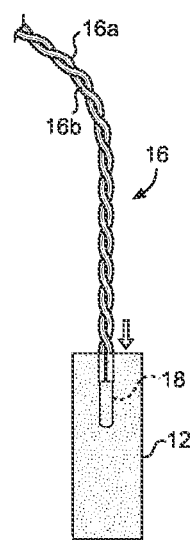

In a first step, as depicted in FIGS. 1A and 1B, the wire set 16 is dipped into a vat or other vessel having the protective material 12 so that the conductor 18 and the immediately adjacent portions of the wire set 16 are coated with the protective material 12. It is preferred that the dipping is performed in a multi-directional motion to ensure that the protective material 12 uniformly coats and covers the conductor 18 in a desired manner to ultimately provide the protective material 12 in a desired shape such as a bead 12a (FIG. 1D). Further, the speed of motion is selected to correspond to the viscosity of the protective material to uniformly coat the conductor which aids in the subsequent formation of the bead 12a in sufficient thickness for desired electrical resistance and protection, yet small enough for desired usage. For medical applications of the temperature sensor 12, such as used to monitor patient temperature, the bead 12a is desirably sufficiently small in dimension so that the conductor 18 coated with the bead 12a can fit inside a 9FR catheter tube, which has an inside diameter of 0.086 inches (2.2 mm).

Figure 1C:
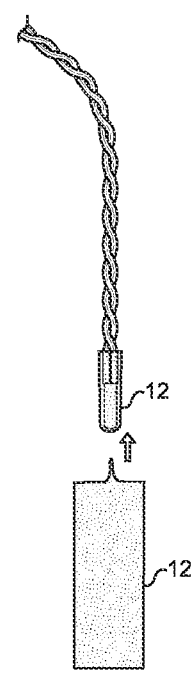
Figure 1D:
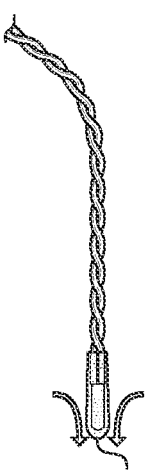

Next, as shown in FIGS. 1C and 1D, the dipped end of the wire set 16/conductor 18 having the bead 12a formed thereon is removed from the vat of the protective material 12 while maintaining the wire set 16 oriented downward as represented by the arrows to allow for flow of the protective material 12 as coated on the conductor 18 to be the formed into and retained on the conductor 18 in the configuration of the bead 12a. In this regard, the formation of the bead 12a is depicted by relative comparison of FIGS. 1C and 1D.

Figure 1F:
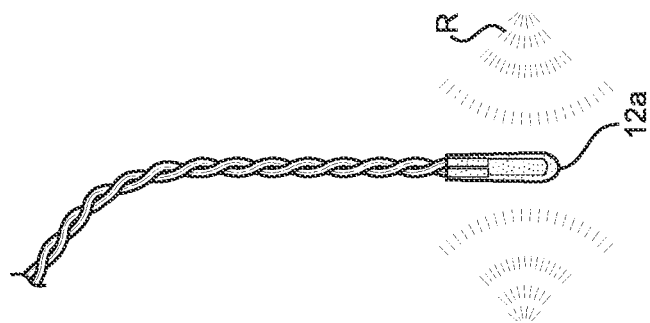
Figure 1E:
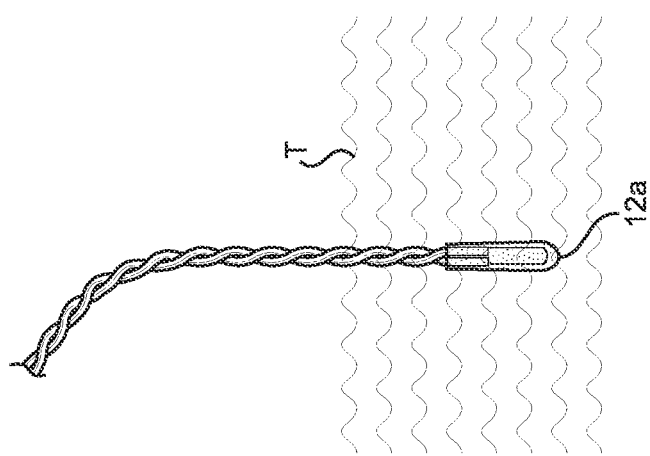

Following this, as depicted in FIG. 1E, the wire set 16 with the bead 12a of protective material is maintained for a period of from about 2 to about 10 seconds at an appropriate ambient temperature T of from about 68 to about 78 degrees F. (20-25.5 degrees C.) to maintain adequate viscosity of the protective material 12 forming the bead 12a to prevent dripping or loss of the bead 12a while awaiting curing. Following this, as depicted in FIG. 1F, curing of the bead 12a of the protective material 12 is accomplished by exposure of the bead 12a to UV or visible light or other optical radiation R suitable for curing of the protective material 12.

The use of a radiation curable adhesive as a protective material according to the disclosure provides significant improvement over prior methods for protecting temperature sensors, such as bonding a molded thermoplastic resin cap over a conductor with epoxy. As will be appreciated, the present method eliminates the need for a molded cap. Further, it eliminates the time consuming and messy operation of curing the epoxy, and the cleanup thereof by trimming away excess epoxy.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical temperature monitoring system, comprising:
   a thermistor comprising an electrical wire set having a conductor at a distal end of the wire set configured to sense temperatures to which the thermistor is exposed;
   an electronic circuit in electrical communication with the thermistor and configured to convert the temperatures sensed by the thermistor to temperature display signals;
   a display in electrical communication with the electronic circuit for receiving the temperature display signals and displaying temperatures corresponding to the temperature display signals; and
   a bead of cured protective material uniformly encapsulating the thermistor, the bead of cured protective material comprising a radiation curable adhesive applied to the distal end of the wire set and the conductor in an uncured state so that the conductor and the adjacent portions of the distal end of the wire set are coated with the protective material in the uncured state and the protective material is then cured to uniformly encapsulate the conductor and the adjacent portions of the distal end of the wire set to form the bead of cured protective material and electrically isolate the conductor.

2. The temperature monitoring system of claim 1, wherein the bead has a largest diameter of about 0.09 inches or less.

3. The temperature monitoring system of claim 1, wherein the radiation curable adhesive has a viscosity of from about 9,000 cP to about 18,000 cP in the uncured state.

4. The temperature monitoring system of claim 1, wherein the radiation curable adhesive comprises an aliphatic urethane acrylate and monomer blend.

5. The temperature monitoring system of claim 1, wherein the radiation curable adhesive is curable by exposure to light.

6. A thermistor, comprising:
an electrical wire set having a pair of wires with a conductor at a distal end of the wires configured to sense temperatures to which the conductor is exposed; and
a bead of protective material uniformly encapsulating the conductor, the protective material comprising a radiation curable adhesive applied to the conductor in an uncured state and then cured to uniformly encapsulate the conductor as the bead and isolate the conductor sufficient to pass a Hi-Pot test at 500 VAC, <0.1 mA.

7. The thermistor of claim 6, wherein the bead has a largest diameter of about 0.09 inches or less.

8. The thermistor of claim 6, wherein the radiation curable adhesive has a viscosity of from about 9,000 cP to about 18,000 cP in the uncured state.

9. The thermistor of claim 6, wherein the radiation curable adhesive comprises an aliphatic urethane acrylate and monomer blend.

10. The thermistor of claim 6, wherein the radiation curable adhesive is curable by exposure to light.

11. A method of making a temperature sensor, comprising the steps of:
providing an electrical wire set having a conductor at a distal end of the wire set configured to sense temperatures to which the conductor is exposed;
providing a protective material comprising a curable adhesive in a liquid uncured state having a viscosity;
dipping the conductor into the protective material at a speed selected for the viscosity of the protective material in the liquid uncured state to uniformly coat the conductor with the protective material;
withdrawing the coated conductor from the protective material at a speed selected for the viscosity of the protective material in the uncured state while maintaining the conductor oriented downward to allow for flow of the protective material as coated on the conductor to be formed into and retained on the conductor in the configuration of a bead;
maintaining the coated conductor in the downward orientation at a temperature selected to maintain adequate viscosity of the protective material forming the bead to maintain the shape of the bead and prevent dripping of the bead; and
curing the bead of the protective material.

12. The method of claim 11, wherein the bead after curing has a largest diameter of about 0.09 inches or less.

13. The method of claim 11, wherein the protective material has a viscosity in the uncured state of from about 9,000 cP to about 18,000 cP.

14. The method of claim 11, wherein the protective material comprises an aliphatic urethane acrylate and monomer blend.

15. The thermistor of claim 11, wherein after curing the bead of protective material electrically isolates the conductor sufficient to pass a Hi-Pot test at 500 VAC, <0.1 mA.

16. The method of claim 11, wherein the protective material is radiation curable and the step of curing the bead of the protective material comprises exposing the bead to radiation.

17. The method of claim 11, wherein the step of dipping the conductor into the protective material comprises dipping the conductor with a multi-directional motion.

* * * * *